(12) United States Patent
Kawa et al.

(10) Patent No.: US 8,080,586 B2
(45) Date of Patent: Dec. 20, 2011

(54) SELF-EMULSIFYING PREPARATIONS

(75) Inventors: Rolf Kawa, Monheim (DE); Ulrich Issberner, Rommerskirchen (DE)

(73) Assignee: Cognis IP Management GmbH, Duesseldorf (DE)

( * ) Notice: Subject to any disclaimer, the term of this patent is extended or adjusted under 35 U.S.C. 154(b) by 1165 days.

(21) Appl. No.: 10/963,857

(22) Filed: Oct. 13, 2004

(65) Prior Publication Data

US 2005/0136081 A1 Jun. 23, 2005

(30) Foreign Application Priority Data

Oct. 15, 2003 (DE) .................................. 103 47 940

(51) Int. Cl.
*A61K 47/00* (2006.01)
(52) U.S. Cl. ......... 514/786; 514/844; 514/938; 424/401
(58) Field of Classification Search .................. 514/786, 514/844, 938; 424/401
See application file for complete search history.

(56) References Cited

U.S. PATENT DOCUMENTS

| | | | | |
|---|---|---|---|---|
| 5,494,938 A | * | 2/1996 | Kawa et al. .................... | 514/786 |
| 5,958,431 A | | 9/1999 | Brancq et al. | |
| 6,800,293 B1 | * | 10/2004 | Farby et al. .................... | 424/401 |
| 2005/0065221 A1 | * | 3/2005 | Schmid et al. .................. | 516/77 |

FOREIGN PATENT DOCUMENTS

| | | |
|---|---|---|
| DE | 198 51 451 | 5/2000 |
| DE | 100 61 420 | 6/2002 |
| EP | 0 554 292 | 12/1994 |
| WO | WO 00/61102 | 10/2000 |
| WO | WO03043725 A1 * | 5/2003 |

OTHER PUBLICATIONS

Lochhead et al., "Encyclopedia of Polymers and Thickeners for Cosmetics", Cosmetics & Toiletries, vol. 108, (May 1993), pp. 95-114, 116-124, 127-130, 132-135.
"Kosmetische Färbemittel", Farbstoffkommission der Deutschen Forschungsgemeinschaft, Verlag Chemie, Weinheim, (1984), pp. 81-106.

* cited by examiner

*Primary Examiner* — Frederick Krass
*Assistant Examiner* — Nannette Holloman
(74) *Attorney, Agent, or Firm* — Diehl Servilla LLC

(57) ABSTRACT

The invention relates to new self-emulsifying preparations containing
(a) 7 to 20% by weight stearyl oligoglycoside,
(b) 7 to 20% by weight cetyl oligoglycoside,
(c) 0.1 to 3% by weight myristyl oligoglycoside,
(d) 0.5 to 7% by weight lauryl oligoglycoside,
(e) 4 to 12% by weight cetyl alcohol,
(f) 10 to 20% by weight stearyl alcohol,
(g) 20 to 30% by weight $C_{16/18}$ partial glycerides containing 58 to 62% by weight monoglyceride and
(h) 20 to 30% by weight $C_{16/18}$ partial glycerides containing 30 to 45% by weight monoglyceride,
with the proviso that the quantities shown add up to 100% by weight with water.

7 Claims, No Drawings

SELF-EMULSIFYING PREPARATIONS

RELATED APPLICATIONS

This application claims priority of German application DE 103 47 940.6 filed Oct. 15, 2003; the entire contents of which application are incorporated herein by reference.

FIELD OF THE INVENTION

This invention relates generally to the cosmetics field and, more particularly, to new self-emulsifying preparations which, even when used in very small quantities, lead to emulsions characterized by high storage and viscosity stability.

PRIOR ART

In recent years, the cosmetic chemist has increasingly acquired high-performance self-emulsifying bases containing "eco-friendly" emulsifiers which, even in very low concentrations, i.e. less than 1% emulsifying constituents, are capable of forming emulsions with long-term stability, even under temperature stress. On the one hand, there are economic motives for this because the cost pressure of the market is becoming ever greater; on the other hand, however, there are also dermatological and ecological reasons. A self-emulsifying base is understood to be a system which already contains the key constituents of an emulsion adapted exactly to one another, namely emulsifiers and waxes as consistency factors, so that—ideally—only suitable oil components (emollients) and optionally auxiliaries need be added to obtain emulsions with long-term stability. Eco-friendly emulsifiers are nonionic structures free from ethylene oxide, emulsifiers of the alkyl polyglucoside type generally being preferred. Corresponding self-emulsifying bases from the prior art, as described in EP 0554292 B1 (Cognis), are unable to satisfy this requirement completely because at least 4% by weight emulsifying constituents, based on the formulation as a whole, are needed for a stable oil-in-water emulsion. If the concentration falls below that level, the danger of phase separation increases dramatically; at the same time, there is a reduction in viscosity.

Accordingly, the problem addressed by the invention was to provide an eco-friendly self-emulsifying base with a far more effective emulsifying performance with which phase- and viscosity-stable oil-in-water emulsions could be produced. More particularly, the invention set out to provide self-emulsifying preparations which, even when used in a concentration of at most 2 and preferably at most 1% by weight, based on the emulsifying constituents, would lead to emulsions that would remain stable for 2 to 3 months, even under temperature stress, and would not undergo any collapse of viscosity, irrespective of the nature of the oil component.

BRIEF DESCRIPTIONS OF THE INVENTION

The present invention relates to new self-emulsifying preparations containing
(a) 7 to 20% by weight stearyl oligoglycoside,
(b) 7 to 20% by weight cetyl oligoglycoside,
(c) 0.1 to 3% by weight myristyl oligoglycoside,
(d) 0.5 to 7% by weight lauryl oligoglycoside,
(e) 4 to 12% by weight cetyl alcohol,
(f) 10 to 20% by weight stearyl alcohol,
(g) 20 to 30% by weight $C_{16/18}$ partial glycerides containing 58 to 62% by weight monoglyceride and
(h) 20 to 30% by weight $C_{16/18}$ partial glycerides containing 30 to 45% by weight monoglyceride,
with the proviso that the quantities shown add up to 100% by weight with water.

It has surprisingly been found that a self-emulsifying base consisting of a special mixture of alkyl oligoglycosides differing in their chain lengths, fatty alcohols and partial glycerides with a defined distribution is capable of forming stable o/w emulsions in which the concentration of emulsifying constituents, based on the formulation as a whole, is less than 2% by weight and, more particularly, less than 1% by weight.

DETAILED DESCRIPTION OF THE INVENTION

Alkyl Oligoglycosides

Alkyl oligoglycosides which form emulsifying components (a), (b), (c) and (d) are known nonionic surfactants corresponding to formula (I):

$$R^1O\text{-}[G]_p \qquad (I)$$

in which $R^1$ is an alkyl group containing 12, 14, 16 or 18 carbon atoms, G is a sugar unit containing 5 or 6 carbon atoms and p is a number of 1 to 10. They may be obtained by the relevant methods of preparative organic chemistry. The alkyl oligoglycosides may be derived from aldoses or ketoses containing 5 or 6 carbon atoms, preferably glucose. Accordingly, the preferred alkyl oligoglycosides are alkyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

Fatty Alcohols

Fatty alcohols which form components (e) and (f) are understood to be primary aliphatic alcohols corresponding to formula (II):

$$R^2OH \qquad (II)$$

in which $R^2$ is a linear alkyl group containing 16 or 18 carbon atoms. Typical examples are cetyl alcohol and stearyl alcohol and technical mixtures thereof, for example the 1:1 mixture cetearyl alcohol.

Partial Glycerides

Partial glycerides, i.e. monoglycerides, diglycerides and technical mixtures thereof, which form components (g) and (h) may also contain small quantities of triglycerides from their production. The partial glycerides preferably correspond to formula (III):

$$\begin{array}{l} CH_2OCOR^3 \\ | \\ CH\text{—}OR^4 \\ | \\ CH_2\text{—}OR^5 \end{array} \qquad (III)$$

in which $R^3CO$ is a linear saturated acyl group containing 16 to 18 carbon atoms, $R^4$ and $R^5$ independently of one another have the same meaning as $R^3CO$ or represent hydrogen, with the proviso that at least one of the two substituents $R^4$ and $R^5$ represents hydrogen. Typical examples are mono- and/or diglycerides based on palmitic and/or stearic acid and technical mixtures thereof. Two different partial glycerides differing in their monoester content are used in accordance with the present invention. A suitable partial glyceride containing 58 to 62% by weight monoglyceride is, in particular, Monomuls® 60-35; a suitable partial glyceride containing 30 to 45% by weight monoglyceride is Cutina® MD (both Cognis Deutschland GmbH & Co. KG).

Commercial Applications

The present invention also relates to the use of the self-emulsifying preparations for the production of cosmetic and/or pharmaceutical compositions in which they may be present in quantities of 0.1 to 8% by weight and preferably 0.5 to 5% by weight, based on the preparation, or 0.1 to 2% by weight, based on the emulsifying constituents present therein.

Cosmetic and/or Pharmaceutical Compositions

The cosmetic and/or pharmaceutical compositions prepared using the self-emulsifying preparations may contain other typical auxiliaries and additives such as, for example, mild surfactants, oil components, emulsifiers, pearlizing waxes, consistency factors, thickeners, superfatting agents, stabilizers, polymers, silicone compounds, fats, waxes, lecithins, phospholipids, UV protection factors, moisturizing components, biogenic agents, antioxidants, deodorizers, antiperspirants, anti-dandruff agents, film formers, swelling agents, insect repellents, self-tanning agents, tyrosine inhibitors (depigmenting agents), hydrotropes, solubilizers, preservatives, perfume oils, dyes and the like.

Surfactants

Suitable surfactants are anionic, nonionic, cationic and/or amphoteric or zwitterionic surfactants which may be present in the preparations in quantities of normally about 1 to 70% by weight, preferably 5 to 50% by weight and more preferably 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkyl hydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, for example Dicaprylyl Carbonate (Cetiol® CC), Guerbet carbonates based on $C_{6-18}$ and preferably $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, for example Dicaprylyl Ether (Cetiol® OE), ring opening products of epoxidized fatty acid esters with polyols, silicone oils (cyclomethicone, silicon methicones, etc.) and/or aliphatic or naphthenic hydrocarbons such as, for example, squalane, squalene or dialkyl cyclohexanes.

Emulsifiers

Suitable emulsifiers are, for example, nonionic surfactants from at least one of the following groups:

products of the addition of 2 to 30 mol ethylene oxide and/or 0 to 5 mol propylene oxide onto linear $C_{8-22}$ fatty alcohols, $C_{12-22}$ fatty acids, alkyl phenols containing 8 to 15 carbon atoms in the alkyl group and alkylamines containing 8 to 22 carbon atoms in the alkyl group;

alkyl and/or alkenyl oligoglycosides containing 8 to 22 carbon atoms in the alk(en)yl group and ethoxylated analogs thereof;

products of the addition of 1 to 15 mol ethylene oxide onto castor oil and/or hydrogenated castor oil;

products of the addition of 15 to 60 mol ethylene oxide onto castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof with 1 to 30 mol ethylene oxide;

partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof with 1 to 30 mol ethylene oxide;

mixed esters of pentaerythritol, fatty acids, citric acid and fatty alcohol and/or mixed esters of fatty acids containing 6 to 22 carbon atoms, methyl glucose and polyols, preferably glycerol or polyglycerol;

mono-, di- and trialkyl phosphates and mono-, di- and/or tri-PEG-alkyl phosphates and salts thereof;

wool wax alcohols;

polysiloxane/polyalkyl/polyether copolymers and corresponding derivatives;

block copolymers, for example Polyethyleneglycol-30 Dipolyhydroxy-stearate;

polymer emulsifiers, for example Pemulen types (TR-1, TR-2) from Goodrich or Cosmedia® SP from Cognis;

polyalkylene glycols and glycerol carbonate.

Alkoxylates

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations.

Alkyl and/or Alkenyl Oligoglycosides

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may also contain small quantities of triglyceride from the production process. Products of the addition of 1 to 30 and preferably 5 to 10 mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triiso-stearate, sorbitan monooleate, sorbitan sesquioleate, sorbitan dioleate, sorbitan trioleate, sorbitan monoerucate, sorbitan sesqui-erucate, sorbitan dierucate, sorbitan trierucate, sorbitan mono-ricinoleate, sorbitan sesquiricinoleate, sorbitan diricinoleate, sorbitan triricinoleate, sorbitan monohydroxystearate, sorbitan sesqui-hydroxystearate, sorbitan dihydroxystearate, sorbitan trihydroxy-stearate, sorbitan monotartrate, sorbitan sesquitartrate, sorbitan ditartrate, sorbitan tritartrate, sorbitan monocitrate, sorbitan sesqui-citrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers

Typical anionic emulsifiers are aliphatic fatty acids containing 12 to 22 carbon atoms such as, for example, palmitic acid, stearic acid or behenic acid and dicarboxylic acids containing 12 to 22 carbon atoms such as, for example, azelaic acid or sebacic acid.

Amphoteric and Cationic Emulsifiers

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum (Keltrol types from Kelco), guar-guar, agar-agar, alginates and tyloses, carboxymethyl cellulose and hydroxyethyl and hydroxypropyl cellulose, also relatively high molecular weight polyethylene glycol mono-esters and diesters of fatty acids, polyacrylates (for example Cosmedia® SP and SPL [Cognis], Carbopols® and Pemulen types [Goodrich]; Synthalens® [Sigma]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate. Other suitable consistency factors are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat poly-peptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacryl-amide/methyl methacrylate/tert-butylaminoethyl methacrylate/2-hydroxy-propyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

UV Protection Factors

UV protection factors in the context of the invention are, for example, organic substances (light filters) which are liquid or crystalline at room temperature and which are capable of absorbing ultraviolet or infrared radiation and of releasing the energy absorbed in the form of longer-wave radiation, for example heat. The UV protection factors are present in quantities of normally 0.1 to 5% by weight and preferably 0.2 to 1% by weight. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives.

Suitable water-soluble substances are 2-phenylbenzimidazole-5-sulfonic acid and alkali metal, alkaline earth metal, ammonium, alkylammonium, alkanolammonium and glucammonium salts thereof;

1H-Benzimidazole-4,6-Disulfonic Acid, 2,2'-(1,4-Phenylene)-bis-, Disodium Salt (Neo Heliopan®);

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789), 2-(4-diethylamino-2-hydroxybenzoyl)-benzoic acid hexyl ester (Uvinul® A Plus), 1-phenyl-3-(4'-isopropylphenyl)-propane-1,3-dione and enamine compounds. The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000, Eusolex® T, Eusolex® T-ECO, Eusolex® T-S, Eusolex® T-Aqua, Eusolex® T45D (all Merck), Uvinul TiO$_2$ (BASF). Suitable hydrophobic coating materials are, above all, silicones and, among these, especially trialkoxyoctylsilanes or simethicones. So-called micro- or nanopigments are preferably used in sun protection products. Micronized zinc oxide, for example in the form of Z-COTE® or Z-COTE HP1®, is preferably used.

Moisturizers

Moisturizers contribute towards further optimizing the sensory properties of the composition and regulate the skin moisture level. At the same time, the low-temperature stability of the preparations according to the invention, particularly in the case of emulsions, is increased. The moisturizers are normally present in a quantity of 0.1 to 15% by weight, preferably 1 to 10% by weight and more particularly 5 to 10% by weight.

According to the invention, suitable moisturizers are inter alia amino acids, pyrrolidone carboxylic acid, lactic acid and salts thereof, lactitol, urea and urea derivatives, uric acid, glucosamine, creatinine, cleavage products of collagen, chitosan or chitosan salts/derivatives and, in particular, polyols and polyol derivatives (for example glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), honey and hydrogenated honey, hydrogenated starch hydrolyzates and mixtures of hydrogenated wheat protein and PEG-20-acetate copolymer. According to the invention, particularly preferred moisturizers are glycerol, diglycerol, triglycerol and butylene glycol.

Biogenic Agents and Antioxidants

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Antioxidants interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and heptathionine sulfoximine) in very small compatible dosages (for example pmol to μmol/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example $ZnO$, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Germ Inhibitors

Basically, suitable germ inhibitors are any substances which act against gram-positive bacteria such as, for example, 4-hydroxybenzoic acid and salts and esters thereof, N-(4-chloro-phenyl)-N'-(3,4-dichlorophenyl)-urea, 2,4,4'-trichloro-2'-hydroxy-diphenylether (triclosan), 4-chloro-3,5-dimethylphenol, 2,2'-methylene-bis-(6-bromo-4-chlorophenol), 3-methyl-4-(1-methyl-ethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Enzyme Inhibitors

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Odor Absorbers

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat.

Antiperspirants

Antiperspirants reduce perspiration and thus counteract underarm wetness and body odor by influencing the activity of the eccrine sweat glands. Aqueous or water-free antiperspirant formulations typically contain the following ingredients:
astringent active principles,
oil components,
nonionic emulsifiers,
co-emulsifiers,
consistency factors,
auxiliaries in the form of, for example, thickeners or complexing agents and/or
non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium penta-chlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example,
inflammation-inhibiting, skin-protecting or pleasant-smelling essential oils,
synthetic skin-protecting agents and/or
oil-soluble perfume oils.
Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-yl methoxyphenyl}-piperazine, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Special Active Components

Suitable insect repellents are N,N-diethyl-m-toluamide, pentane-1,2-diol or Ethyl Butylacetylaminopropionate. A suitable self-tanning agent is dihydroxyacetone. Suitable tyrosine inhibitors which prevent the formation of melanin and are used in depigmenting preparations are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are
glycerol;
alkylene glycols such as, for example, ethylene glycol, diethylene glycol, propylene glycol, butylene glycol, hexylene glycol and poly-ethylene glycols with an average molecular weight of 100 to 1000 dalton;
technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid, the silver complexes known by the name of Surfacine® and the other classes of compounds listed in Appendix 6, Parts A and B of the Kosmetikverordnung ("Cosmetics Directive").

Perfume Oils and Aromas

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable aromas are, for example, peppermint oil, spearmint oil, aniseed oil, Japanese anise oil, caraway oil, eucalyptus oil, fennel oil, citrus oil, wintergreen oil, clove oil, menthol and the like.

Dyes

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS(C.I. 69800) and madder lake (C.I. 58000). Luminol may also be present as a luminescent dye. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular preparation. The preparations may be produced by standard hot or cold processes and are preferably produced by the phase inversion temperature method.

EXAMPLES

Cosmetic emulsions were prepared with the two self-emulsifying bases A (invention) and C (comparison) described in the following (see Table 1) and were evaluated in regard to viscosity and phase stability as a function of temperature and time. The two self-emulsifying bases were prepared by suitably stirring the constituents homogeneously in the molten state at 80° C., followed by cooling.

TABLE 1

Composition of self-emulsifying cosmetic bases (quantities in % by weight)

| Composition | A | C |
|---|---|---|
| Stearyl glucoside | 12.0 | — |
| Cetyl glucoside | 12.0 | 38.0 |
| Myristyl glucoside | 0.3 | — |
| Lauryl glucoside | 0.7 | — |
| Cetyl alcohol | 9.0 | 4.0 |
| Stearyl alcohol | 15.0 | 4.0 |
| $C_{16/18}$ partial glycerides containing 58 to 62% by weight monoglyceride | 25.0 | 54.0 |
| $C_{16/18}$ partial glycerides containing 35 to 45% by weight monoglyceride | 23.0 | — |
| Water | | to 100 |

The cosmetic emulsions (based on a 200 g laboratory batch) were produced by the hot method. To this end, the oil phase was heated to 80° C. and the polymer component Carbopol® 940 was homogeneously dispersed therein. The water phase—also heated to 80° C.—was then slowly added to the oil phase with stirring. The emulsion was cooled with stirring to 40° C., adjusted to pH 7 and then further cooled to 30° C. During cooling (between 45 and 65° C.), the emulsion was homogenized for 2 minutes using a suitable rotor/stator system (for example IKA Ultra Turrax® T 50). The composition of the cosmetic emulsion is shown in Table 2.

The stability of the emulsions was visually evaluated for 1 to 12 weeks using a school marking scale where (1)=stable, (2)=slight separation, (3)=separations, (4)=distinct separations and (5)=divisions. Viscosity was determined by the Brookfield method in an RVF viscosimeter, spindle 5, 10 r.p.m., 23° C. The performance results are set out in Table 2.

Example 1 corresponds to the invention, Examples C1 and C2 are intended for comparison. The concentration of emulsifying constituents was ca. 0.6% by weight in Example 1, ca. 4% by weight in Example C1 and ca. 2% by weight in Example C2, based in each case on the formulation as a whole.

TABLE 2

Cosmetic emulsions and their properties (quantities in % by weight)

| Composition/performance | C1 | C2 | 1 |
|---|---|---|---|
| Oil phase | | | |
| Self-emulsifying base C | 10 | 5 | — |
| Self-emulsifying base A | — | — | 2.5 |
| Myritol ® 331 | | 3 | |
| Cocoglycerides | | | |
| Cetiol ® OE | | 4 | |
| Dicaprylyl Ether | | | |
| Cegesoft ® PS 6 | | 5 | |
| Olus (EU), Vegetable Oil (non-EU) | | | |
| Carbopol ® 940 | | | 0.1 |
| Carbomer | | | |
| Water phase | | | |
| Glycerol | | | 3.0 |
| Water, preservative, KOH | to 100 and pH 7.0 | | |
| Viscosity [Pas] | | | |
| Start | 20 | 12.8 | 22 |
| after 1 week | 21.2 | 11.2 | 22.4 |
| after 2 weeks | 22 | 9.6 | 22.4 |

TABLE 2-continued

Cosmetic emulsions and their properties (quantities in % by weight)

| Composition/performance | C1 | C2 | 1 |
|---|---|---|---|
| after 4 weeks | 21.6 | 6.4 | 22.4 |
| after 8 weeks | 20.4 | 4.0 | 23 |
| after 12 weeks | 20 | 1.6 | 23 |
| Phase stability (−5/+2−/+40° C.) | | | |
| after 1 week | 1/1/1 | 1/1/1 | 1/1/1 |
| after 2 weeks | 1/1/1 | 2/2/3 | 1/1/1 |
| after 4 weeks | 1/1/1 | 3/2/4 | 1/1/1 |
| after 8 weeks | 1/1/1 | 4/3/4 | 1/1/1 |
| after 12 weeks | 1/1/1 | 4/4/5 | 1/1/1 |

The use of the preparation according to the invention in a quantity of well below 1% by weight, based on the emulsifying components, leads to emulsions which are viscosity- and phase-stable over a period of 3 months at temperatures of −5 to +40° C. In order to achieve a comparable effect, the comparison product has to be used in 6 times the quantity. However, if the concentration of the comparison product is reduced to about 3 times the quantity, the viscosity collapses and complete phase separation occurs in a short time.

A number of Formulation Examples are presented in the following Table. Quantities are expressed in % by weight of the commercially available substances in the composition as a whole. The letter L stands for lotion, C for cream and S for spray.

TABLE 3

O/W sun protection emulsions

| Component | 1 L | 2 C | 3 S | 4 L | 5 C | 6 L | 7 L | 8 C | 9 L | 10 C | 11 L |
|---|---|---|---|---|---|---|---|---|---|---|---|
| Example A (invention) | 2 | 2.5 | 2.5 | 1 | 2.5 | 2.5 | 2.5 | 2 | 2.5 | 1.7 | 1.5 |
| Eumulgin ® VL 75 | | | | | | | | | | | 2 |
| Eumulgin ® B2 | 0.5 | | | | | | | | | | |
| Tween ® 60 | | | | | 0.2 | | | | | | |
| Myrj ® 51 | | | | | 0.5 | | | | | | |
| Cutina ® E 24 | | | | | 0.1 | | | | | | |
| Hostaphat ® KL 340 N | | | | | | | | | 0.6 | | |
| Lanette ® E | | | | 0.2 | | | | | | | |
| Amphisol ® K | | | | | | | | | | 1 | |
| Sodium stearate | | | | | | 1 | | | | | |
| Emulgade ® PL 68/50 | | | 1 | | | | | | | | |
| Tego ® Care 450 | | | | | | | | | | 1 | |
| Cutina ® MD | 2 | | | 2 | | | 2 | | | 6 | |
| Lanette ® 14 | 1 | | | 1 | | | | 2 | | | 2 |
| Lanette ® O | 1 | 6 | | | 5 | 2 | | 2 | | | |
| Cosmedia ® DC | 1 | 1.5 | | 1 | 1 | | 2 | 2 | | | 2 |
| Antaron ® V 216 | | | 2 | | | 1.5 | | | 1 | 1 | |
| Emery ® 1780 | | | | | | 0.5 | 0.5 | | | | |
| Lanolin, anhydrous USP | | | | | | | | 5 | | | |
| Myritol ® PC | | | | | 5 | | | | | | |
| Myritol ® 331 | 5 | | 8 | | | 6 | | 10 | | 2 | |
| Finsolv ® TN | | | 1 | | | | | 1 | 8 | | |
| Cetiol ® CC | | 2 | 5 | | | 4 | 4 | 2 | | 2 | |
| Cetiol ® OE | | | 3 | | | | | | | 2 | 3 |
| Dow Corning DC ® 244 | 4 | | 1 | | 5 | | | 2 | | | 2 |
| Dow Corning DC ® 2502 | | 1 | | | 2 | | | | | | |
| Squatol ® S | | | | | | | 4 | | | | |
| Silikonöl Wacker AK ® 350 | | 2 | | | | | | | | | |
| Cetiol ® 868 | | | | | | 2 | | 4 | | | 7 |
| Cetiol ® J 600 | | | | | | 3 | 2 | | | 5 | |
| Mineral oil | | | | 9 | | | | | | | |
| Cetiol ® B | | | 1 | | | | | | | 2 | |
| Eutanol ® G | | | | | 2 | | | | 4 | | |
| Eutanol ® G 16 | 4 | | | | | 4 | | | | | |
| Cetiol ® PGL | | | 5 | | | | | | | 5 | |
| Almond oil | | | 2 | | | 1 | | | | | |
| Photonyl ® LS | | | | | 2 | | | | | | 2 |

TABLE 3-continued

O/W sun protection emulsions

| Component | 1 L | 2 C | 3 S | 4 L | 5 C | 6 L | 7 L | 8 C | 9 L | 10 C | 11 L |
|---|---|---|---|---|---|---|---|---|---|---|---|
| Panthenol | | | | | | 1 | | | | | |
| Bisabolol | | | | | | 0.2 | | | | | |
| Tocopherol/Tocopherylacetate | | | | | | 1 | | | | | |
| Photonyl ® LS | | | | | | | | | | | |
| Neo Heliopan ® AP (Na salt) | | 1 | | | | | | | 1 | | |
| Neo Heliopan ® Hydro (Na salt) | 2 | | 2.2 | | | | | | 1 | | |
| Neo Heliopan ® 303 | 3 | 5 | 9 | 4 | | | | | | | |
| Neo Heliopan ® BB | | | | | 1 | | | | | | 2 |
| Neo Heliopan ® MBC | 2 | | | 3 | | 2 | 2 | 2 | | | 1 |
| Neo Heliopan ® OS | | | | | | | | | 10 | 7 | |
| Neo Heliopan ® E 1000 | | 7.5 | | 6 | | | | | | | 6 |
| Neo Heliopan ® AV | | | 7.5 | | | 7.5 | 4 | 5 | | | |
| Uvinul ® A PLUS | | | | 2 | 1 | | | | | | |
| Uvinul ® T 150 | 2 | | | 2.5 | | | | 1 | | | |
| Parsol ® 1789 | | 1 | 1 | | | | 2 | | 2 | 2 | |
| Zinc oxide NDM | 10 | | 5 | | | 10 | | 3 | | 5 | 4 |
| Eusolex ® T 2000 | | | | | 5 | | 3 | 3 | | | 4 |
| Veegum ® Ultra | 1.5 | | 0.75 | | | | | 1 | 1 | | |
| Keltrol ® T | 0.5 | | 0.25 | | | | | 0.5 | 0.5 | | |
| Cosmedia ® SP | | 0.5 | | | 0.5 | | 0.2 | 0.2 | | 0.2 | 0.2 |
| Carbopol ® 980 | | | | 0.2 | | 0.2 | | | 0.1 | 0.3 | 0.2 |
| Ethanol | | | | | | | | | | 10 | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservative, NaOH, water | | | | | | q.s. to 100 | | | | | |

TABLE 4

O/W sun protection emulsions

| Component | 12 L | 13 C | 14 L | 15 C | 16 L | 17 C | 18 S | 19 C | 20 C | 21 L | 22 L |
|---|---|---|---|---|---|---|---|---|---|---|---|
| Example A (invention) | 2 | 1.8 | 2.5 | 1.5 | 1 | 2 | 2.5 | 3 | 2.0 | 1.5 | 1.5 |
| Eumulgin ® VL 75 | | | | | 1.8 | | | | | | |
| Eumulgin ® B2 | | | | | | | | | | 0.2 | |
| Tween ® 60 | | | | | | | | | | 0.3 | |
| Cutina ® E 24 | | | | 0.5 | | | | | | | |
| Hostaphat ® KL 340 N | | | | | | | | | | | 0.5 |
| Lanette ® E | | | | | | | 0.1 | | 0.5 | | |
| Amphisol ® K | 0.5 | | | | | | 1 | | | | |
| Sodium stearate | | | | | 1 | | | | | | |
| Emulgade ® PL 68/50 | | 1.5 | | | | | | | | | |
| Tego ® Care 450 | | | | | | | | | 0.3 | | |
| Cutina ® MD | 1 | | | 4 | 1 | 3 | | | | | 1 |
| Lanette ® 14 | | 2 | | | | | | | | 1 | |
| Lanette ® O | | | | 2 | | | | 2 | 1 | 1 | |
| Allianz ® OPT | 1 | | | 1 | 1 | | | 2 | | | 2 |
| Cosmedia ® DC | | 1.5 | 2 | | | 1.5 | 2 | | | 1.5 | 1.5 |
| Emery ® 1780 | | | | | 1 | 1 | | | | | |
| Lanolin, anhydrous, USP | | | | | | 1 | 1 | | | | |
| Myritol ® PC | | | | | | | | | 5 | | |
| Myritol ® 331 | 12 | | 12 | | | 8 | 8 | | | 10 | 8 |
| Finsolv ® TN | | | | | 5 | | | 3 | 3 | | |
| Cetiol ® CC | 6 | | 6 | | | 5 | 5 | | | | |
| Cetiol ® OE | | | | | 2 | | | | | | 2 |
| Dow Corning DC ® 244 | | 2 | | | 1 | | | | | | |
| Dow Corning DC ® 2502 | | 1 | | | 1 | | | 3 | | | |
| Ceraphyl ® 45 | | | | | | | | | | 2 | 2 |
| Silikonöl Wacker AK ® 350 | | | | | 1 | | | | | | |
| Cetiol ® 868 | | 2 | | | | | | | | | |
| Cetiol ® J 600 | | 2 | | | | | | | | | |
| Mineral oil | | | | 10 | | | | | | | |
| Cetiol ® B | 4 | | 4 | | | | | 4 | | | |
| Eutanol ® G | | 3 | | | 3 | | | | | | |
| Eutanol ® G 16 S | 10 | | | | | | | | | | |
| Cetiol ® PGL | | | | | | | | | 2 | | |
| Photonyl ® LS | | | | | | | | | | 2 | |
| Panthenol | | | | | 1 | | | | | | |
| Bisabolol | | | | | 0.2 | | | | | | |

TABLE 4-continued

| | O/W sun protection emulsions | | | | | | | | | | |
|---|---|---|---|---|---|---|---|---|---|---|---|
| Component | 12 L | 13 C | 14 L | 15 C | 16 L | 17 C | 18 S | 19 C | 20 C | 21 L | 22 L |
| Tocopherol/Tocopheryl acetate | | | | | | 1 | | | | | |
| Neo Heliopan ® Hydro (Na salt) | | | | | | | | | | 3 | |
| Eusolex ® OCR | 6 | | 9 | | 5 | 7 | 9 | | 4 | | 7 |
| Neo Heliopan ® AP (Na salt) | | | | 0.5 | | 1 | | | | | |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | | 7 | | |
| Neo Heliopan ® E1000 | | 4 | | | | | | 5 | | | |
| Neo Heliopan ® AV | | 4 | 7.5 | 5 | | | 2 | 5 | 4 | 7.5 | |
| Uvinul ® A PLUS | | | | | 1 | | 2 | | | | |
| Uvinul ® T 150 | 1 | | | | | | | | 1.3 | 1 | 1 |
| Parsol ® 1789 | 1 | | | | | 7 | 5 | | 2 | | 1 |
| Z-Cote ® HP 1 | 7 | 2 | 5 | | | 7 | 5 | | 6 | 2 | |
| Eusolex ® T 2000 | 5 | 2 | | | 10 | | | 10 | | 2 | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Cosmedia ® SP | | | 0.2 | 0.3 | | | 0.1 | | | 0.2 | |
| Pemulen ® TR 2 | | 0.3 | | 0.3 | | | | 0.2 | | | 0.3 |
| Ethanol | | 5 | | 8 | | | | | | | |
| Butylene glycol | 1 | | | 3 | 3 | | | | | 8 | 1 |
| Glycerin | 2 | 4 | 3 | 3 | | 3 | 3 | 3 | 5 | | 3 |
| Water/preservative/NaOH | | | | | to 100/q.s./q.s. | | | | | | |

TABLE 5

| | W/O care emulsions | | | | | | | | | | |
|---|---|---|---|---|---|---|---|---|---|---|---|
| Component | 23 C | 24 C | 25 C | 26 L | 27 C | 28 L | 29 L | 30 C | 31 L | 32 C | 33 C |
| Example A (invention) | 2.5 | 2 | 3 | 3 | 2 | 2 | 2.5 | 1.7 | 2.5 | 1.5 | 1.2 |
| Eumulgin ® VL 75 | | | | | | | | | | 1.5 | |
| Dehymuls ® PGPH | | 0.6 | | | | | | | | | |
| General ® R | | | 0.5 | | | | | | | | |
| Eumulgin ® B2 | | | 0.1 | | | | | | | | |
| Tween ® 60 | | | | | 0.2 | | | | | | |
| Cutina ® E 24 | | | | | 0.2 | | | | | | |
| Hostaphat ® KL 340 N | | | | | | | | | 0.5 | | |
| Lanette ® E | | | | | | | | 0.6 | | | |
| Amphisol ® K | | 0.2 | | | | | | | | | |
| Sodium stearate | | | | | 0.5 | | | | | | |
| Emulgade ® PL 68/50 | | | | | | | | | | | 1.2 |
| Tego ® Care CG | 0.7 | | | | | | | | | | |
| Tego ® Care 450 | | | | | 0.4 | | | | | | |
| Cutina ® MD | | 1 | | | 5 | | 2 | | 6 | | |
| Lanette ® 14 | | | | 1 | | | 4 | | | 4 | |
| Lanette ® O | 4.5 | | 4 | | 1 | 2 | | | | 2 | |
| Novata ® AB | | 1 | | | | | | | | 1 | |
| Emery ® 1780 | | | | | 0.5 | 0.5 | | | | | |
| Lanolin, anhydrous, USP | | | | | | | 1.1 | | | | |
| Cosmedia ® DC | | 1.5 | 2 | | | 1.5 | 2 | | 1.5 | 1.5 | |
| Cetiol ® SB 45 | | | 1.5 | | | | 2 | | | | |
| Cegesoft ® C 17 | | | | | | | | | | 2 | |
| Myritol ® PC | | | | | 5 | | | | | | |
| Myritol ® 331 | 2 | 5 | 5 | | | 6 | | 12 | | | |
| Finsolv ® TN | | | 2 | | | 2 | | | 8 | | |
| Cetiol ® CC | 4 | 6 | | | | 4 | 4 | | | 5 | |
| Cetiol ® OE | | | | 5 | | | | | 4 | 3 | |
| Dow Corning DC ® 245 | | | 2 | | 5 | 1 | | | | | |
| Dow Corning DC ® 2502 | | | | | 2 | 1 | | | | 5 | |
| Prisorine ® 3758 | | | | | | 1 | | | | | |
| Silikonöl Wacker AK ® 350 | 0.5 | 0.5 | 0.5 | | | 1 | 4 | | | | |
| Cetiol ® 868 | | | | | 2 | | 4 | | | | |
| Cetiol ® J 600 | 2 | | 3 | | 3 | 2 | | | | 5 | |
| Ceraphyl ® 45 | | | | | | | 3 | | | | |
| Mineral oil | | | | 9 | | | | | | | |
| Cetiol ® SN | | | 5 | | | | | | | | |
| Cetiol ® B | | | | | | | | 4 | | 2 | |
| Eutanol ® G | | 2 | | 3 | | | | | | | |
| Cetiol ® PGL | | | | | | | | | 5 | 5 | |

TABLE 5-continued

W/O care emulsions

| Component | 23 C | 24 C | 25 C | 26 L | 27 C | 28 L | 29 L | 30 C | 31 L | 32 C | 33 C |
|---|---|---|---|---|---|---|---|---|---|---|---|
| Dry Flo ® Plus | 5 | | | | | | 1 | | | | |
| SFE 839 | 5 | | | | | | | | | | 2 |
| Almond oil | | | | | | 1 | | | | | |
| Insect Repellent ® 3535 | | 2 | 4 | | 2 | | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | 1 | | | | | |
| Bisabolol | | | | | | 0.2 | | | | | |
| Tocopherol/Tocopheryl acetate | | | | | | 1 | | | | | |
| Veegum ® ultra | | | | | | | | | 1 | | |
| Keltrol ® T | | | | 0.4 | | | | | 0.5 | | |
| Cosmedia ® SP | | | 0.3 | | 0.2 | 0.2 | | | | 0.2 | 0.3 |
| Pemulen ® TR 2 | 0.3 | | | | | | | 0.3 | | | |
| Carbopol ® Ultrez 10 | | | | 0.3 | | | 0.2 | | | | |
| Ethanol | | | | | | | | | | 10 | |
| Butylene glycol | | | | 4 | 3 | | 2 | 5 | 2 | | |
| Glycerin | 2 | 5 | 5 | | 3 | 3 | 2 | | 4 | | 3 |
| Water, preservative, NaOH | to 100, q.s., pH 6.5-7.5 | | | | | | | | | | |

TABLE 6

O/W care emulsions

| Component | 34 C | 35 C | 36 L | 37 C | 38 L | 39 C | 40 C | 41 L | 42 L | 43 L | 44 C |
|---|---|---|---|---|---|---|---|---|---|---|---|
| Example A (invention) | 2 | 2 | 1 | 3 | 2.5 | 2 | 3.8 | 1.2 | 2.5 | 1.5 | 0.8 |
| Eumulgin ® VL 75 | | | | | | | | | | | 1 |
| Generol ® R | | | | | | 0.3 | | | | | |
| Eumulgin ® B2 | | | | | | | | | | 1 | |
| Tween ® 60 | | | | | | | | | | 1 | |
| Cutina ® E 24 | | | | 0.5 | | | | | | | |
| Lanette ® E | 0.5 | | | | | | | | | | |
| Amphisol ® K | | 0.5 | | | | | | | | | |
| Sodium stearate | | | | | 1 | | | | | | |
| Emulgade ® PL 68/50 | | | | | | | | 1 | | | |
| Tego ® Care 450 | | | | | | | | | 1 | | |
| Cutina ® MD | 3 | 1 | | 4 | | | | | | | |
| Lanette ® 14 | | 2 | | | 1 | | | 2 | | 1 | |
| Lanette ® O | 2 | | | 2 | | 3 | 1 | | 1 | 1 | 6 |
| Novata ® AB | | | | | | | | | 1 | 1 | |
| Emery ® 1780 | | | | | | | | | | | 0.5 |
| Lanolin, anhydrous, USP | | | | | | 4 | | | | | |
| Cosmedia ® DC | | | 1 | | | 1.5 | | | 1 | 1 | |
| Cetiol ® SB 45 | | | | | | | 2 | | | | |
| Cegesoft ® C 17 | 4 | | | | | | | | | | |
| Myritol ® PC | 6 | | | | | 5 | | | 5 | | |
| Myritol ® 331 | 5 | | 5 | | | | 7 | | | 10 | 3 |
| Finsolv ® TN | | 5 | | 4 | 5 | | | 3 | 3 | | 1 |
| Cetiol ® CC | | | 8 | 6 | | | 4 | 3 | | | 2 |
| Cetiol ® OE | | | | | 2 | | 2 | | 5 | | |
| Dow Corning DC ® 245 | | 2 | | | 1 | 8 | | | | 8 | 2 |
| Dow Corning DC ® 2502 | | 1 | | 1 | | | | | | | 3 |
| Prisorine ® 3758 | 3 | | | | | | | | | | 2 |
| Silikonöl Wacker AK ® 350 | | | | | | 1 | | | | | 1 |
| Cetiol ® 868 | | 2 | | | | | | | | | |
| Cetiol ® J 600 | | 2 | | 2 | | | | | | | |
| Ceraphyl ® 45 | | | | | | | 3 | | | | |
| Cetiol ® SN | | | | 5 | | | | | | | |
| Cetiol ® B | | | | | | 5 | | 4 | | | 3 |
| Eutanol ® G | | 3 | | | 5 | | | | | | |
| Cetiol ® PGL | | | | | | | | 5 | 2 | | |
| Dry Flo ® Plus | | 1 | | | | | | | | | 1 |
| SFE 839 | 1 | 1 | | | | | | | | | |
| Almond oil | | | | | | 2 | | | | | |
| Photonyl ® LS | | | | | | 2 | | | | | |
| Panthenol | | | | | | 1 | | | | | |
| Bisabolol | | | | | | 0.2 | | | | | |
| Tocopherol/Tocopheryl acetate | | | | | | 1 | | | | | |
| Veegum ® Ultra | | | | | | | | | 1 | | |
| Keltrol ® T | | | | | | | | | 0.5 | | |

TABLE 6-continued

| | O/W care emulsions | | | | | | | | | |
|---|---|---|---|---|---|---|---|---|---|---|
| Component | 34 C | 35 C | 36 L | 37 C | 38 L | 39 C | 40 C | 41 L | 42 L | 43 L | 44 C |
| Cosmedia ® SP | 0.1 | | 1 | | 0.2 | 0.2 | 0.2 | 0.2 | | | 0.5 |
| Carbopol ® ETD 2001 | | 0.3 | | 0.3 | | | | | | | |
| Pemulen ® TR 2 | | | | | | 0.3 | | | | | |
| Ethanol | | 5 | | 8 | | | | | | | 10 |
| Butylene glycol | 5 | | | 3 | 3 | | | | | 8 | |
| Glycerin | 2 | 4 | 3 | 3 | | 7 | 5 | 3 | 5 | | |
| Water, preservative, NaOH | | | | | to 100, q.s., (pH 6.5-7.5) | | | | | | |

We claim:
1. A self-emulsifying base composition consisting of:
   (a) 7 to 20% by weight stearyl oligoglycoside,
   (b) 7 to 20% by weight cetyl oligoglycoside,
   (c) 0.1 to 3% by weight myristyl oligoglycoside,
   (d) 0.5 to 7% by weight lauryl oligoglycoside,
   (e) 4 to 12% by weight cetyl alcohol,
   (f) 10 to 20% by weight stearyl alcohol,
   (g) 20 to 30% by weight $C_{16/18}$ partial glycerides containing 58 to 62% by weight monoglyceride,
   (h) 20 to 30% by weight $C_{16/18}$ partial glycerides containing 30 to 45% by weight monoglyceride; and
   (i) water to 100%.
2. The self-emulsifying base composition of claim 1, wherein oligoglycosides (a) to (d) conform to formula (I):

$$R^1O\text{-}[G]_p \qquad (I)$$

wherein $R^1$ is an alkyl group containing 12, 14, 16 or 18 carbon atoms, G is a sugar unit containing 5 or 6 carbon atoms and p is a number of 1 to 10.

3. The self-emulsifying base composition of claim 1, wherein the partial glycerides (g) and (h) conform to formula (III):

wherein $R^3CO$ is a linear saturated acyl group containing 16 or 18 carbon atoms, $R^4$ and $R^5$ independently of one another have the same meaning as $R^3CO$ or represent hydrogen, wherein, at least one of the substituents $R^4$ and $R^5$ independently represents hydrogen.

4. The self-emulsifying base composition of claim 2, wherein the partial glycerides (g) and (h) conform to formula (III):

wherein $R^3CO$ is a linear saturated acyl group containing 16 or 18 carbon atoms, $R^4$ and $R^5$ independently of one another have the same meaning as $R^3CO$ or represent hydrogen, wherein, at least one of the substituents $R^4$ and $R^5$ independently represents hydrogen.

5. A member selected from the group consisting of cosmetic preparations and pharmaceutical preparations comprising the self-emulsifying base composition of claim 1.

6. A member selected from the group consisting of cosmetic preparations and pharmaceutical preparations comprising from 0.1 to 8% by weight of the self-emulsifying base composition of claim 1, based on the weight of the preparation.

7. A member selected from the group consisting of cosmetic preparations and pharmaceutical preparations comprising from 0.1% to 2% of the self-emulsifying base composition of claim 1, based on the weight of the preparation.

* * * * *